(12) United States Patent
de Rijke

(10) Patent No.: US 6,265,619 B1
(45) Date of Patent: *Jul. 24, 2001

(54) OXYGENATES AND PROCESSES FOR THEIR MANUFACTURE

(75) Inventor: Jan Martin de Rijke, Oostvoorne (NL)

(73) Assignee: Exxon Chemical Patents Inc., Houston, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/860,639

(22) PCT Filed: Jan. 17, 1996

(86) PCT No.: PCT/EP96/00162

§ 371 Date: Feb. 23, 1998

§ 102(e) Date: Feb. 23, 1998

(87) PCT Pub. No.: WO96/22264

PCT Pub. Date: Jul. 25, 1996

(51) Int. Cl.$^7$ .................................................. C07C 45/50
(52) U.S. Cl. ........................ 568/451; 568/454; 568/840; 568/880; 562/512; 560/129
(58) Field of Search ..................... 568/387, 388, 568/390, 395, 396, 398, 451, 454, 880, 882, 883, 840; 562/512; 560/129

(56) References Cited

U.S. PATENT DOCUMENTS

| | | | |
|---|---|---|---|
| 2,731,503 | 1/1956 | Mattox et al. | 260/638 |
| 2,852,563 | 9/1958 | Hagemeyer et al. | 260/601 |
| 3,527,809 | 9/1970 | Pruett et al. | 260/604 |
| 3,917,661 | 11/1975 | Pruett et al. | 260/410.9 |
| 4,148,830 | 4/1979 | Pruett et al. | 260/604 |
| 4,247,486 | 1/1981 | Brewester et al. | 568/454 |
| 4,262,142 | 4/1981 | Sherman, Jr. et al. | 568/454 |
| 4,283,562 | 8/1981 | Billig et al. | 568/454 |
| 4,426,542 | 1/1984 | Barker et al. | 568/883 |

FOREIGN PATENT DOCUMENTS

| | | |
|---|---|---|
| 2111360 | 6/1994 | (CA). |
| 4243524 * | 6/1994 | (DE). |
| 052999 | 6/1982 | (EP). |
| 1120277 | 7/1968 | (GB). |
| 1387657 | 3/1975 | (GB). |
| WO 93/24437 | 12/1993 | (WO). |

OTHER PUBLICATIONS

J. Falbe, "New Syntheses w/Carbon Monoxide", Chapter 1—Hydroformylation, Oxo Synthesis, Roelen Reaction, by B. Cornils, pp. 1–225, Springer–Verlag, New York, 1980.

Keulemans et al., "The Structure Of The Formylation (OXO) Products Obtained From Olefines And Watergas", vol. 67, pp. 298–308, Recueil, (1948).

Falbe, J. and Cornils B. "Polyacrylic Compounds to Mercury" in Uhlmann's Encyclopedia of Industrial Chemistry, pp. 443–452, vol. 19, 4th Edition, 1980, (English Translation).

Wender et al., "Organic Synthesis via Metal Carbonyls", vol. 2, pp. 233–296, Wiley–Interscience Publication, 1990.

A. Papa, "Propanols" in Uhlmann's Encyclopedia of Industrial Chemistry, pp. 173–183, vol. A22, 5th Edition, 1993.

* cited by examiner

Primary Examiner—Sreeni Padmanabhan
(74) Attorney, Agent, or Firm—Douglas J Collins

(57) ABSTRACT

Alcohols suitable for plasticizer ester manufacture and acids are made by cofeeding olefins to oxonation, aldolizing the resulting aldehyde and hydrogenating the resulting unsaturated aldehydes, optionally dehydrating a part of the alcohol thereby made and returning the resulting olefin to oxonation, or oxidizing the aldehydes.

18 Claims, 7 Drawing Sheets

OXYGENATES AND PROCESSES FOR THEIR MANUFACTURE

This is the U.S. National Stage Application of PCT/EP96/00162 filed Jan. 7, 1996 now WO 96/22264 published Jul. 25, 1996.

FIELD OF THE INVENTION

This invention relates to a process for the manufacture of aldehydes, alcohols, acids, and esters, the use of the latter as synthetic lubricants, as plasticizers, to polymeric compositions plasticized by the esters, and to products made from the compositions.

BACKGROUND OF THE INVENTION

The esters of 2-ethylhexanol, especially the phthalate, are among the most commonly used plasticizers. The alcohol is obtainable by, for example, subjecting propene to hydroformylation, dimerizing the resulting butanal by the aldol reaction, a term which is used throughout this specification, including the claims, as including the subsequent dehydration to an unsaturated aldehyde, and hydrogenating the resulting aldehyde to form a saturated alcohol.

The propene, produced for example by a steam cracking plant, has to be purified before hydroformylation, and its cost as feedstock is increased as a result.

There accordingly remains a need for an alternative route to commercially useful organic molecules, and more especially one that is capable, if desired, of producing a single isomeric product or a preponderant proportion of one or two isomers.

BRIEF SUMMARY OF THE INVENTION

The present invention provides a process for the manufacture of at least one higher aldehyde, higher alcohol, or a higher acid, from a lower hydrocarbon, which comprises hydroformylating two different ethylenically unsaturated hydrocarbons to form a first aldehyde and a second aldehyde, the hydrocarbons being hydroformylated separately or in admixture and, if the latter, if desired or required at least partially separating the first aldehyde from the second aldehyde, subjecting the first aldehyde, if desired in admixture with the second, to aldolization, hydrogenating at least a portion of the resulting unsaturated aldehyde or aldehydes to form a corresponding higher alcohol or alcohols, and, if only a portion is so hydrogenated, optionally selectively hydrogenating a further portion of the unsaturated aldehyde to form a corresponding saturated higher aldehyde, optionally oxidizing it to form a corresponding higher acid, optionally dehydrating a portion of the higher alcohol or of the higher alcohols to form at least one ethylenically unsaturated hydrocarbon and returning it to hydroformylation, and optionally recovering the second aldehyde as higher aldehyde, hydrogenating it to form a higher alcohol, or oxidizing it to form a higher acid.

Advantageously, the process includes returning unsaturated hydrocarbon produced by dehydration to oxonation. It is within the scope of the invention to return unsaturated aldehyde to aldolization, although this is not at present preferred.

More especially, in a first aspect, the present invention provides a process comprising (a) subjecting a composition comprising two ethylenically unsaturated hydrocarbons having differing numbers of carbon atoms, carbon monoxide, and hydrogen to hydroformylation conditions to form a composition comprising at least a lower aldehyde and a higher aldehyde, (b) at least partially separating the lower and higher aldehydes, to form a lower aldehyde-containing composition and a higher aldehyde-containing composition, (c) subjecting the lower aldehyde-containing composition to aldol condensation, and, optionally, (d) hydrogenating the unsaturated aldehyde resulting from the aldol condensation to form a first alcohol and, optionally, dehydrating at least a portion of the first alcohol to form an ethylenically unsaturated hydrocarbon, and optionally returning the resulting ethylenically unsaturated hydrocarbon to hydroformylation, and optionally hydrogenating the higher aldehyde-containing composition to form a second alcohol and optionally esterifying the first, the second, or both the first and second alcohols separately or together.

Advantageously the two unsaturated hydrocarbons subjected to hydroformylation are such that the resulting lower and higher aldehydes are readily separable by, for example, distillation.

Except where the context otherwise requires, the features of the first aspect said below to be advantageous are advantageous in all aspects of the invention, especially the specifically listed succeeding aspects.

Advantageously, return of the ethylenically unsaturated hydrocarbon resulting from dehydration to the hydroformylation step in the process takes place when it has the same number of carbon atoms as one of the feedstock hydrocarbons and preferably, when there are only two, the hydrocarbon having the higher number of carbon atoms. If it differs from both the feedstock hydrocarbons it is advantageously transferred to a parallel operation, carrying out a process on a hydrocarbon feed to which it is identical. It is, however, although not presently preferred, within the scope of the invention to carry out the process with unsaturated hydrocarbons having three or more different carbon numbers.

DETAILED DESCRIPTION OF THE INVENTION

As examples of unsaturated hydrocarbons to be treated by the process of the invention there may be mentioned, more especially, olefins, and advantageously olefins having from 2 to 20 carbon atoms.

The invention is especially applicable to treating a mixture of a lower, $C_2$ to $C_4$, and a higher, $C_5$ to $C_{20}$, olefin. As lower olefins there may be mentioned ethylene, propene, n-butene and 2-methylpropene. As higher olefins there may be especially be mentioned single isomeric olefin feeds, for example, pentene-1, hexene-1 and their higher homologues, or mixtures of linear and branched olefin isomers predominantly of the same carbon number. An example of the latter is a hexene feed, which may contain 2-methylpentene-1, 2-methylpentene-2-, cis- and trans-4-methylpentene-2, 4-methylpentene-1, cis- and trans-hexene-3, cis- and trans-hexene-2, 2,3-dimethylbutene-2, 2-ethylbutene-1 and trans-3-methylpentene-2. Usually olefin feeds of this nature also contain varying amounts of the corresponding alkanes.

The invention is more especially applicable to treating a mixture of ethylene and higher e.g., $C_5$ and above, alkenes, especially hexenes, especially 2-methylpentene-1.

On subjecting such a mixture to hydroformylation, a mixture of $C_3$ and $C_7$ saturated aldehydes results; on subjecting the $C_3$ aldehyde to aldolization an unsaturated $C_6$ aldehyde results. This may, if desired, be selectively hydrogenated to a $C_6$ saturated aldehyde, which may in turn be hydrogenated to a $C_6$ alcohol, or oxidized to form a $C_6$ acid. The alcohol, or a portion thereof, may be dehydrated to hexene, which will largely be 2-methylpentene-1 and -2, which may be recycled to the hydroformylation stage. Accordingly, from the $C_6$ and $C_7$ saturated aldehydes there may be produced the corresponding alcohols and their esters, or the corresponding acids and their esters.

The invention accordingly provides a means of obtaining $C_6$ and $C_7$ products from ethylene as the sole hydrocarbon starting material.

In an advantageous embodiment of the first aspect of the invention, there is accordingly provided a process comprising hydroformylating a composition comprising ethylene and a 2-methylpentene, separating the resulting $C_3$ aldehyde and $C_7$ aldehydes, aldolizing the $C_3$ aldehyde, hydrogenating the resulting $C_6$ unsaturated aldehyde to form an alcohol, dehydrating the alcohol to form a composition comprising a 2-methylpentene, returning the composition to the hydroformylation stage, and recovering a product comprising a $C_7$ aldehyde.

The 2-methylpentene may be a mixture of isomers, advantageously predominantly 2-methylpentene-1 and -2.

U.S. Pat. No. 4,426,542 discloses dimerizing propene, oxonating the resulting hexenes to heptanals, hydrogenating to heptanois, dehydrating to heptenes and oxonating the heptenes, the octanals resulting being aldolized in turn with hexanal and hydrogenated to form inter alia a $C_{14}$ alcohol.

U.S. Pat. No. 4,262,142 discloses the low pressure hydroformylation of mixtures of ethylene and an alpha-olefin having from 3 to 20 carbon atoms using a rhodium-based catalyst, while GB-A-1,120,277 discloses hydroformylating ethylene and propene under high pressure using a cobalt-based catalyst. In the U.S. patent, it is pointed out that under the conditions of the British patent propene conversion is adversely affected by the presence of ethylene; this disadvantage is avoided when a rhodium-based catalyst is employed. In the hydroformylation process of the present invention, however, a cobalt catalyst is advantageously used.

The composition treated in step (a) of the first aspect of the present invention comprises as essential ingredients carbon monoxide, hydrogen, and two unsaturated hydrocarbons. In a preferred embodiment of the invention, one hydrocarbon is ethylene, and the second hydrocarbon is provided by recycling, as described above, either from the same process or a similar process using different starting materials. For clarity, the invention will be described in more detail below with reference solely to ethylene and a second, recycled, hydrocarbon, but it will be appreciated that, mutatis mutandis, the procedures apply to other feedstocks.

The components of the composition not obtained by recycling may be obtained by numerous methods, including mixing pure $C_2H_4$, CO and $H_2$, mixing purified commercially produced $C_2H_4$ with purified synthesis gas (syngas) or as the direct or purified product of a steam cracking furnace. The composition is, however, conveniently a dilute multicomponent syn gas (DMCS) stream, by "dilute" being meant that the stream has not been completely purified by the removal of diluents, e.g., methane and ethane, that do not take part in the hydroformylation reaction. The stream may result from treatment of natural gas, e.g., from the mixture of a first stream containing CO and $H_2$ produced by a conventional partial oxidation (POX) technology and a second stream containing ethylene. Ethylene may be obtained from any of a number of sources, inter alia, from ethane, which is also obtainable from natural gas; another route to ethylene is by methane pyrolysis.

Depending on the source, the DMCS will contain, as indicated above, $H_2$, CO and one or both $C_2$ unsaturated hydrocarbons, and in addition different neutral and undesired species.

The DMCS composition, as far as concerns neutral and essential components, is advantageously as follows in molar terms:

CO: 5 to 33%, preferably 10 to 33%, of gas.

$C_2H_4$: up to 100% of CO.

$H_2$: from, at minimum, the molar equivalent of the ethylenically unsaturated species, to a maximum of 60% of DMCS. A preferred maximum is twice the molar equivalent of ethylenically unsaturated species.

Sum of alkanes, $CO_2$, $N_2$, and other inerts, e.g., Ar, and $H_2O$: 0 to 70%, preferably 0 to 40%.

The literature contains many references to hydroformylation of pure ethylene with syngas; literature sources include "New Syntheses with Carbon Monoxide", Ed. J. Falbe, Springer Verlag, New York, 1980, especially the Chapter "Hydroformylation, Oxo Synthesis, Roelen Reaction" by B. Cornils; and U.S. Pat. Nos. 3,527,809, 3,917,661 and 4,148,830, which describe an oil-soluble phosphine-modified rhodium catalyst, the disclosures of all these documents being incorporated herein by reference.

Advantageously, however, the catalyst is a cobalt catalyst, e.g., hydrocobaltcarbonyl or one of its precursors, e.g., as dicobaltoctacarbonyl. Hydrocobaltcarbonyl is volatile and may be introduced to the hydroformylation zone in the gas flow with the other gaseous components. The catalyst is, however, also soluble in liquid hydrocarbons and is advantageously introduced to the hydroformylation zone with the higher olefin feed. It is also possible to introduce the catalyst in the form of a solution in an oily solvent or a mixture of such solvents, for example aliphatic and aromatic hydrocarbons (e.g., heptanes, cyclohexane, toluene), esters (e.g., dioctyl phthalate), ethers and polyethers (e.g., tetrahydrofuran, and tetraglyme), aldehydes (e.g., propanal, butanal or higher homologues), alcohols (e.g., propanol, butanol, or higher homologues), or the condensation products of oxo product aldehydes. Another method of introducing the catalyst to the hydroformnylation zone is in the form of an aqueous solution of a light carboxylic acid, e.g., formic, acetic, or propionic acid, when the active cobalt species form under the prevailing conditions.

Hydroformylation is advantageously conducted at a temperature in the range from 40 to 200° C., more advantageously from 80 to 180° C., and preferably in the range from 90 to 155° C.

Hydroformylation may be effected in a single unit, or two or more units. In the latter case, some or all of one olefin, usually the lighter, is conveniently introduced into a downstream unit.

When a lighter olefin is introduced in a downstream unit, the liquid product from an upstream unit, already containing catalyst, serves as a diluent and catalyst carrier for the higher olefin, obviating the necessity for a separate solvent.

The reaction is advantageously conducted at a pressure in the range of 0.05 to 50 MPa (absolute), and preferably in the range of about 0.1 to 30 MPa with a partial pressure of carbon monoxide advantageously not greater than 50% of the total pressure.

Advantageously, the proportions of carbon monoxide, hydrogen, ethylene, and the second olefin in the feed to the oxo reactor at the foregoing pressures are maintained as follows: Co from about 1 to 50 mol %, preferably about 1 to 35 mol %; $H_2$ from about 1 to 98 mol %, preferably about 10 to 90 mol %; ethylene and the second olefin in combination from about 0.1 to 35 mol %, preferably about 1 to 35 mol %.

The reaction may be conducted either in a batch mode or, preferably, on a continuous basis. In a continuous mode residence times advantageously up to 4 hours, and preferably from 30 minutes to 2 hours, is conveniently used.

Since the catalytic oxo conversion process takes place in the liquid phase and the reactants may be gaseous compounds, a high contact surface area between the gas and liquid phases is desirable to avoid mass transfer limitations. A high contact surface area between the catalyst solution and the gas phase may be ensured in any suitable manner, for example, by stirring in a batch autoclave operation. Several types of units used to effect hydroformylation depend on the presence of a liquid phase inside the reactor to absorb the heat of reaction and to transfer it to a cooling device. With a higher olefin present in the feed there is no need for a solvent to form this liquid phase, especially not if a portion of the lighter olefin is introduced into a downstream unit. This is an important advantage of the aspects of the present invention employing co-feeding of olefins to an oxonation zone.

In a continuous operation the reactor feed gas may be contacted with the liquid higher olefin feed containing the catalyst in, for example, reactors which effectively form a continuous-flow stirred reactor. Examples of this type of reactor are gas-lift loop reactors, using either an external or internal loop. Another possible reactor configuration is a long narrow tube, submerged in a cooling medium, whereby high contact surface area between the gas and liquid is obtained by establishing a highly turbulent flow regime. Good contact between the catalyst and the gas feed may also be ensured by dispersing the solution of the catalyst on a high surface area support, a technique well known in the art as supported liquid phase catalysis.

One of several techniques may be used for the removal of solubilized cobalt catalyst from the reactor product. The oxo product may be contacted with an alkaline solution, for example, of sodium hydroxide, whereby the cobalt catalyst is transferred to the aqueous phase and forms a water soluble cobalt carbonyl salt. By treating this with a strong acid, for example sulphuric acid, the cobalt catalyst transfers back into its active form and becomes volatile hydrocobaltcarbonyl, which may either be returned to the hydroformylation zone with the gas feed or absorbed in the liquid feed. This method has, however, the disadvantage that a continuous waste water stream is being generated, which needs to be treated further before it can be discharged. Advantageously, therefore, a closed cycle method is employed. By treating the oxo product with air in the presence of an aqueous solution of a light carboyxlic acid, the cobalt catalyst is transferred to the aqueous phase in the form of a water soluble salt. The resulting solution may either be reintroduced directly in the hydroformylation zone, or sent to an outboard unit, in which the cobalt catalyst is restored to its active form in a preformer and absorbed in the higher olefin feed. The depleted water phase is then returned and re-used to recontact the oxo product in the presence of air, as described in International Appication WO 93/24437, the disclosure of which is incorporated herein by reference.

Any unreacted gaseous components remaining in the oxo product are advantageously flashed off. With the appropriate flash conditions (elevated temperature and close to atmospheric pressure), propanal may be flashed off with this offgas and condensed out. Alternatively alkanal may be distilled out of the degassed product.

An alkanal, e.g., propanal, separated as described above, forms the starting material for stage (c) of this aspect of the process according to the invention, the aldol condensation.

The condensation of two molecules of an aldehyde to form an aldol, usually followed immediately by dehydration, to form an unsaturated aidehyde with twice the original number of carbon atoms (or the sum of the carbon atoms of the two aldehydes if they are different) is well known, as are the conditions required to effect the condensation. In general, moderately elevated temperatures, e.g., from 40° C. to 200° C., and pressures, e.g., from 0.01 to 2 MPa, preferably from 0.1 to 2 MPa, are used, in the presence of a catalyst, either acidic or, preferably, basic. Although organic bases may be used, a, preferably strong, inorganic base, for example an alkali metal hydroxide, is preferred, advantageously in the form of an aqueous solution. Alternatively, a heterogenous catalyst may be used, e.g., $TiO_2$, a basic zeolite, or a chemically bound sulphonic acid, for example, that sold under the trade mark Deloxan ASP by Degussa. The above conditions apply generally to the aldol process steps of the present invention; under the preferred conditions dehydration is very fast and essentially complete.

Aldolization catalyst, advantageously in the form of an aqueous solution, is fed into the aldolization zone; since aldolization produces water, the catalyst and some of the product water are advantageously separated and the concentrated solution returned to the aldolization zone.

Selective hydrogenation of the unsaturation of the aldol product, leaving the carbonyl group unaffected, may be carried out using any of the catalysts known per se for that purpose. As examples of suitable hydrogenation catalysts, there may be mentioned palladium, e.g., a supported palladium catalyst, using, for example, an alumina or carbon support, under relatively mild conditions, e.g., a hydrogen pressure of up to 3, preferably between 0.5 and 2.0, MPa, and a temperature within the range of 80 to 200° C. optionally in an inert solvent. Suitable solvents include aliphatic, alicyclic and aromatic hydrocarbons or oxygenated solvents, for example, alcohols and ethers. This procedure is advantageously used if the desired end product is the corresponding acid, or if it is desired to recycle saturated aldehyde to the aldolization stage.

When the desired end product is a carboxylic acid, oxidation of any saturated aldehyde produced by this process as a separate product may be carried out by any method known per se, i.e., practised in the art or described in the literature. Oxidation is conveniently carried out using oxygen, if desired or required in the presence of a catalyst. As catalyst there may be mentioned a solution containing metallic cations, e.g., copper, cobalt or manganese.

If the desired product is the saturated alcohol-then more vigorous hydrogenation conditions may if desired be employed, hydrogenation of the ethylenic unsaturation and reduction of the carbonyl group taking place at the same time. For this purpose, the reaction may be carried out under conditions and in the presence of catalyst systems known per se. For example, the catalyst may be Ni, Raney Ni, Co, partially reduced copper oxides, copper/zinc oxides, copper chromite, alone or in combination with cobalt and nickel catalysts, Ni/Mo; Ni/W; Co/Mo or Mo on carbon, optionally in their sulphided form, or combinations thereof. The conditions may include, for example, a hydrogen pressure from 2 to 30 MPa and a temperature in the range of 100 to 240°

C. More specifically, a hydrogen pressure in the range of 3.5 to 6.5 MPa, a temperature in the range of 120° C. to 240° C., and a residence time within the range of 0.5 to 4 hours, are preferred, conditions within these ranges being especially preferred if a copper chromite catalyst, preferably with a Ni or Pd catalyst in series, is used.

Dehydration of the alcohol resulting from hydrogenation of the aldol product may then follow. This may be accomplished, for example, at sub-atmospheric pressures, at a temperature in the range of 200° C. to 350° C., over a heterogenous catalyst, e.g., alumina, advantageously silica-free alumina, silica, Ni on alumina, a supported mineral acid, e.g., phosphoric acid on silica or alumina, or over an acidic ion-exchange resin. Alternatively, there may be used homogenous dehydration, by heating in the presence of a water-abstracting agent, e.g., sulphuric acid, a bisulphate, phosphoric acid, zinc chloride, or a sulphonic, especially benzene or a naphthalene sulphonic, acid.

In a second aspect, the invention provides a process for the manufacture of a higher alcohol, the process comprising (a) subjecting a composition comprising a lower ethylenically unsaturated hydrocarbon, carbon monoxide, and hydrogen to hydroformylation conditions to form a composition comprising a lower aldehyde, (b) subjecting a first portion of the lower aldehyde-containing composition to aldol condensation, (c) hydrogenating the unsaturated higher aldehyde resulting from aldol condensation to form a lower alcohol, (d) dehydrating the lower alcohol to form a higher unsaturated hydrocarbon, (e) subjecting a composition comprising the higher unsaturated hydrocarbon, carbon monoxide, and hydrogen to hydroformylation conditions to form a composition comprising a saturated higher aldehyde, (f) subjecting the saturated higher aldehyde and a second portion of the lower aldehyde to cross-aldolization, and (g) hydrogenating the unsaturated cross-aldolization aldehyde product to form the higher alcohol.

As examples of lower ethylenically unsaturated hydrocarbons to be used as feedstock to the process there may be mentioned, more especially, olefins and advantageously olefins having from 2 to 20 carbon atoms, especially ethylene.

On subjecting ethylene to the process of the second aspect of the invention, the lower aldehyde is propanal, the unsaturated higher aldehyde resulting from aldolization is a hexenal, primarily 2-methyl-2-pentenal, the lower alcohol is a hexanol, primarily 2-methyl pentanol, and the higher unsaturated hydrocarbon is a hexene, primarily 2-methylpentene. Oxonation of the hexene yields heptanals, primarily 3- and 5-methylhexanal, and the cross-aldolization product is a mixture of unsaturated and saturated aldehydes in the $C_3$ to $C_{14}$ range.

In any aldolization of two or more different aldehydes, a number of different reactions may take place. In general, a smaller aldehyde is more reactive in the conditions advantageously used in the process of all aspects of the present invention than a larger, in part because of its higher solubility in the aqueous catalyst-containing phase; further a linear or a less-branched aldehyde is more reactive than a branched or more branched aldehyde (an α-branched aldehyde being specifically less reactive); accordingly where, as in the present aspect, it is desired to achieve "cross-aldolization" of $C_7$ and $C_3$ aldehydes, to yield a $C_{10}$ aldehyde, primarily 2,5- and 2,7-dimethyl-2-octenals, it is desirable to minimize condensation of two $C_3$ molecules. To this end, the $C_7$ aldehyde is advantageously maintained in stoichiometric excess relative to the $C_3$ aldehyde, and preferably in a molar ratio of at least 1.5:1.

This ratio determines the relative sizes of the first and second portions of the lower aldehyde composition.

Hydrogenation of the cross-aldolization product yields a mixture of products, including 2,5- and 2,7-dimethyloctanols.

In this second aspect of the invention, in which the preferred lower hydrocarbon is ethylene, the composition treated in step (a) may, for example, be obtained as described above with reference to step (a) of the first aspect, and the catalyst may, for example, be a rhodium or cobalt-containing catalyst also as described above. In an advantageous embodiment of the second aspect of the invention, the process is operated in a semi-continuous manner, in which the second portion of the lower aldehyde and the higher unsaturated hydrocarbon are stored temporarily, the feed of lower hydrocarbon to the oxonation zone is halted, and replaced by the higher unsaturated hydrocarbon, and the resulting saturated higher aldehyde is fed together with the second portion of the lower aldehyde to the aldolization zone. This phase may be continued until the stores of materials are exhausted, when the first phase of the process may be resumed. This makes it possible to use the same oxo and aldol reactors for steps (a) and (e) and (b) and (f), if desired.

While for lower aldehyde manufacture a low pressure rhodium-catalysed process may be used, as described, for example, in U.S. Pat. Nos. 4,283,562, 4,247,486, and British Patent No. 1387657, this catalyst system is not optimal for use with branched higher olefins. Accordingly, where the same oxo reactor and process are to be used for steps (a) and (e), the higher pressure rhodium or cobalt catalyst procedures are preferred, those being described in, for example, Falbe, J. "Carbon Monoxide in Organic Synthesis" (1970), Falbe, J. and Cornils B. in Uhlmann (4th Edition, 1980) 19, 443, and Wender, I. and Pino, P., Organic Synthesis via Metal Carbonyls (1977) 2, 233, the disclosures of all of which are incorporated herein by reference.

If a cobalt catalyst is employed then, in all aspects of the invention, it is advantageously recovered and recycled by the procedure described in International Application WO 93/24437, mentioned above. The reactivated cobalt species produced by this procedure may be fed directly to the reactor when the lower hydrocarbon is being oxonated or absorbed in the higher hydrocarbon feed when that is being oxonated, before being fed to the reactor.

In all aspects of the invention, a substantial fraction by weight of the final product may originate from the syngas feedstock, and hence from natural gas, making for economical aldehyde, alcohol, acid, and hence ester, production.

In a third aspect, the invention provides a process comprising (a) subjecting a composition comprising a first ethylenically unsaturated hydrocarbon, carbon monoxide, and hydrogen to hydroformylation conditions to form a composition comprising a first aldehyde, (b) separately subjecting a composition comprising a second ethylenically unsaturated hydrocarbon, carbon monoxide, and hydrogen to hydroformylation conditions to form a composition comprising a second aldehyde, (c) combining the compositions comprising the first and second aldehydes, subjecting the combined compositions to cross-aldolization, and hydrogenating the unsaturated cross-aldolization aldehyde product to form a higher alcohol.

In a fourth aspect, the invention provides a process comprising
(a) subjecting a composition comprising first and second ethylenically unsaturated hydrocarbons, carbon monoxide, and hydrogen to hydroformylation conditions to form a composition comprising at least a first aldehyde and a second aldehyde,
(b) subjecting the aldehyde-comprising composition to aldol condensation to form a composition comprising a least a self-aldolization product of the first aldehyde and a cross-aldolization product of the first and second aldehydes,
(c) hydrogenating the aldolization product composition to form a composition comprising alcohols,
(d) separating the resulting alcohols, and
(e) optionally dehydrating the alcohol derived from the self-aldolization of the first aldehyde and returning the resulting ethylenically unsaturated hydrocarbon to hydroformylation.

Advantageously, the first hydrocarbon is a lower hydrocarbon and the second is a higher hydrocarbon; advantageously, as in the first aspect, the ethylenically unsaturated hydrocarbon resulting from dehydration is the second, higher, hydrocarbon.

In a fifth aspect of the invention, which may especially conveniently be combined with the fourth, only a portion of the composition comprising at least first and second aldehydes is fed to aldolization, and a further portion is fed to distillation to yield separate compositions comprising the individual aldehydes.

For example, when the first hydrocarbon is ethylene, and the second is propene, the separative distillation yields propanal and iso- and n-butanal. Accordingly the process makes it possible to produce light aldehydes in the same plant as and together with a wide range of alcohols. Other examples of combinations of light hydrocarbons which make effective use of this possibility are combinations of any two or more of ethylene, propene, and n- and iso-butene, yielding, for example, $C_3$ to $C_5$ aldehydes and $C_3$ to $C_{15}$ alcohols.

In a sixth aspect, which may especially conveniently be combined with the fifth, a mixture of first and second aldehydes is subjected to aldolization, and a portion of the resulting lower unsaturated aldehyde is returned to the aldolization zone. This facilitates the production of a wide range of aldehydes, and hence alcohols, downstream.

For example, when the first and second hydrocarbons are ethylene and propene, the lower unsaturated aldehyde is 2-methyl-2-pentenal, cross-aldolization of this with the first and second aldehydes and their self- and cross-aldolization products yields, on hydrogenation, alcohols with from 6 to 10 carbon atoms, while unreacted lower and higher aldehydes yield alcohols with three and four carbon atoms.

In a seventh aspect, particular use is made of the fact that under oxonation conditions, especially when carried out under high pressure in the presence of a rhodium or cobalt carbonyl catalyst, e.g., the hydridotetracarbonyl or di(cobalt)octacarbonyl, isomerization of the double bond tends to occur. This makes it possible to employ olefin feedstocks which, prima facie, would not be amenable to oxonation and, in turn, makes it possible to employ, as a source for producing an olefin feedstock by dehydration, an alcohol that similarly would appear to be unsuitable.

For example, in accordance with rules set out in a paper by Keulemans, et al., Rec. Trav. Chim Pay-Bas, 67, 298 (1948) 2,3-dimethylbutene-2 is not capable of adding a carbonyl group at any carbon atom (each methyl group is adjacent to a quaternary carbon atom, a forbidden access point). In practice, however, double bond isomerization allows hydroformylation to take place at a methyl group, albeit at a reaction rate slower than for other isomers. This isomerization makes possible the use of secondary and tertiary alcohols, as well as primary alcohols, as olefin sources. Since such materials are often produced as by-products in other processes, for example, 2-propanol, sec- and t-butanol, and are presently regarded as of relatively low value, a process that can use them as starting materials has considerable advantages.

In accordance with the seventh aspect, therefore, the invention provides a process in which at least two ethylenically unsaturated hydrocarbons, each advantageously having from 2 to 21 carbon atoms, are hydroformylated, the resulting aldehydes are at least partially separated, at least one aldehyde is aldolized, the resulting unsaturated aldehyde is or aldehydes are hydrogenated to form saturated alcohols, the alcohols are at least partially separated, and at least one alcohol is dehydrated to an ethylenically unsaturated hydrocarbon and subjected to hydroformylation, the alcohol subjected to dehydration being a separated alcohol, an alcohol originating from outside the process, or a mixture of such alcohols.

As examples of processes in accordance with this aspect, there may be mentioned:

A. 2-methylpropanol, a by-product from n-butanol production, is dehydrated to isobutene and co-fed with ethylene to oxonation. Al portion of the resulting 3-methylbutanal and propanal is aldolized to form a mixture of $C_6$, $C_8$ and $C_{10}$ unsaturated aldehydes, and the aldol product combined pith another portion of $C_3$ and $C_5$ aldehydes, hydrogenated, and distilled to form primary alcohols in the $C_3$ to $C_{10}$ range.

B. If, in A above, more $C_9$ is required, the $C_8$ alcohol may be dehydrated and recycled, or 3-octanol from an external source may be dehydrated, oxonated, hydrogenated to $C_9$ alcohol and recovered.

C. A mixture of primary, secondary, and tertiary $C_5$ alcohols may be dehydrated, oxonated, and the resulting $C_6$ aldehydes separated. The primary $C_6$ aldehyde is aldolized, the $C_{12}$ aldehyde is hydrogenated to give a mixture of $C_{12}$ primary alcohols.

D. A mixture of $C_3$ to $C_5$ alcohols from methane carbonylation may be dehydrated, oxonated, cross-aldolized, hydrogenated and distilled to give a range of $C_4$ to $C_{12}$ alcohols.

E. Ethanol, e.g., from fermentation of vegetable material, and 2-methyl-pentanol may be dehydrated, the resulting olefins are oxonated and aldolized in admixture and hydrogenated to yield n-propanol, 2-methylpentanol (part of which may be returned to dehydration) and $C_7$, $C_{10}$, and $C_{14}$ alcohols.

F. A mixture of 2-methylbutenes may be oxonated, part of the resulting $C_6$ aldehyde aldolized, and the whole hydrogenated to $C_6$ and $C_{12}$ alcohols.

Dehydration of the $C_{12}$ alcohol, oxonation of the resulting olefin and part cross-aldolized with $C_6$ aldehyde and hydrogenated, yields $C_{13}$ and $C_{19}$ alcohols. This procedure may be repeated as required.

It will be appreciated that it is within the scope of the invention to employ all or part of one aspect in conjunction with all or part of any other or others to the extent that the procedures are compatible.

As indicated above, the saturated alcohols produced by the processes of the invention are valuable intermediates in the manufacture of esters suitable for use as plasticizers and synthetic lubricants, lubricant components, hydraulic fluids and drilling fluids, by reaction with appropriate acids, for example, by reaction with monobasic or polybasic, e.g., tribasic or more especially dibasic acids, or where appropriate their derivatives, e.g., anhydrides, or by transesterification with other, e.g., methyl, esters. The acids produced by the process of the invention have similar uses. The branched $C_7$ acid produced by the process of the invention has especial utility in the formation, with a polyol, of an ester suitable for use as a refrigerant lubricant.

The acid used for forming an ester with an alcohol produced by the process of the invention may be inorganic or organic; if the latter, carboxylic acids are preferred. Among organic acids, aromatic acids are preferred for plasticizer manufacture, although aliphatic acids are also employed. As examples of acids, phthalic (1,2-benzenedicarboxylic), isophthalic, terephthalic, adipic, fumaric, azelaic, sebacic, trimellitic, pyromellitic, and phosphoric acids may be mentioned. Esters with monobasic and dibasic acids are preferred for lubricants and lubricant components; advantageously the resulting esters contain from 15 to 40 carbon atoms.

The esters may be produced by methods known per se or described in the literature from the alcohol and the relevant acid or, preferably, where appropriate, the anhydride, optionally in the presence of a solvent. Elevated temperatures and reduced pressures are generally employed to drive the reaction toward completion by removal of the water produced. Catalysts may be employed. Suitable catalysts include, for example, a titanium catalyst e.g., a tetraalkyl titanate, especially tetra-iso-propyl or tetraoctyl ortho titanate, or a sulphonic acid, e.g., p-toluene sulphonic acid or methylsulphonic acid. Any catalyst present in the reaction product may be removed by alkali treatment and water washing. Advantageously, the alcohol is used in slight, e.g., about 25%, molar excess relative to the number of acid groups in the acid.

The esters may be used as a plasticizer for numerous polymers, for example, cellulose acetate; homo- and copolymers of aromatic vinyl compounds e.g., styrene, or of vinyl esters with carboxylic acids e.g., ethylene/vinyl acetate copolymers; halogen-containing polymers, especially vinyl chloride homo- and copolymers, more especially those copolymers with vinyl esters of carboxylic acid, esters of unsaturated carboxylic acids and/or olefins; nitrile rubbers; and post-chlorinated vinyl chloride polymers. Poly(vinyl chloride) is of especial interest.

The proportion of plasticizer may vary within wide limits, but is generally 10 to 200 parts by weight per 100 parts of polymer, more especially 20 to 100 parts per 100.

The esters may be used alone as plasticizer, or in admixture with other plasticizers, for example, dibutyl, dipentyl, dihexyl, diheptyl, dioctyl, dinonyl, didecyl, diundecyl, didodecyl, ditridecyl phthalates, trimellitates or adipates, or butyl benzyl phthalate, or mixtures thereof. If used in admixture, it is the total proportion of plasticizer that is advantageously within the ranges given above.

The plasticized polymeric compositions may be made up in numerous forms and have various end-uses. For example, they may be in the form of a dryblend, a paste, or a plastisol, depending on the grade of the resin employed. They may be used, for example, as coatings, in dipping, spraying, rotational moulding, or self-supporting films and sheets, and may readily be foamed. End uses include flooring materials, wall coverings, moulded products, upholstery materials, leather substitutes, electrical insulation and coated fabrics.

BRIEF DESCRIPTION OF THE DRAWINGS

Various embodiments of the process of the invention will now be described in greater detail by way of example only with reference to the accompanying drawings, in which.

Each of FIGS. 1 to 6 is a schematic flow diagram of a process for the manufacture of at least one aldehyde, alcohol, or acid from an olefin.

Figure 1:
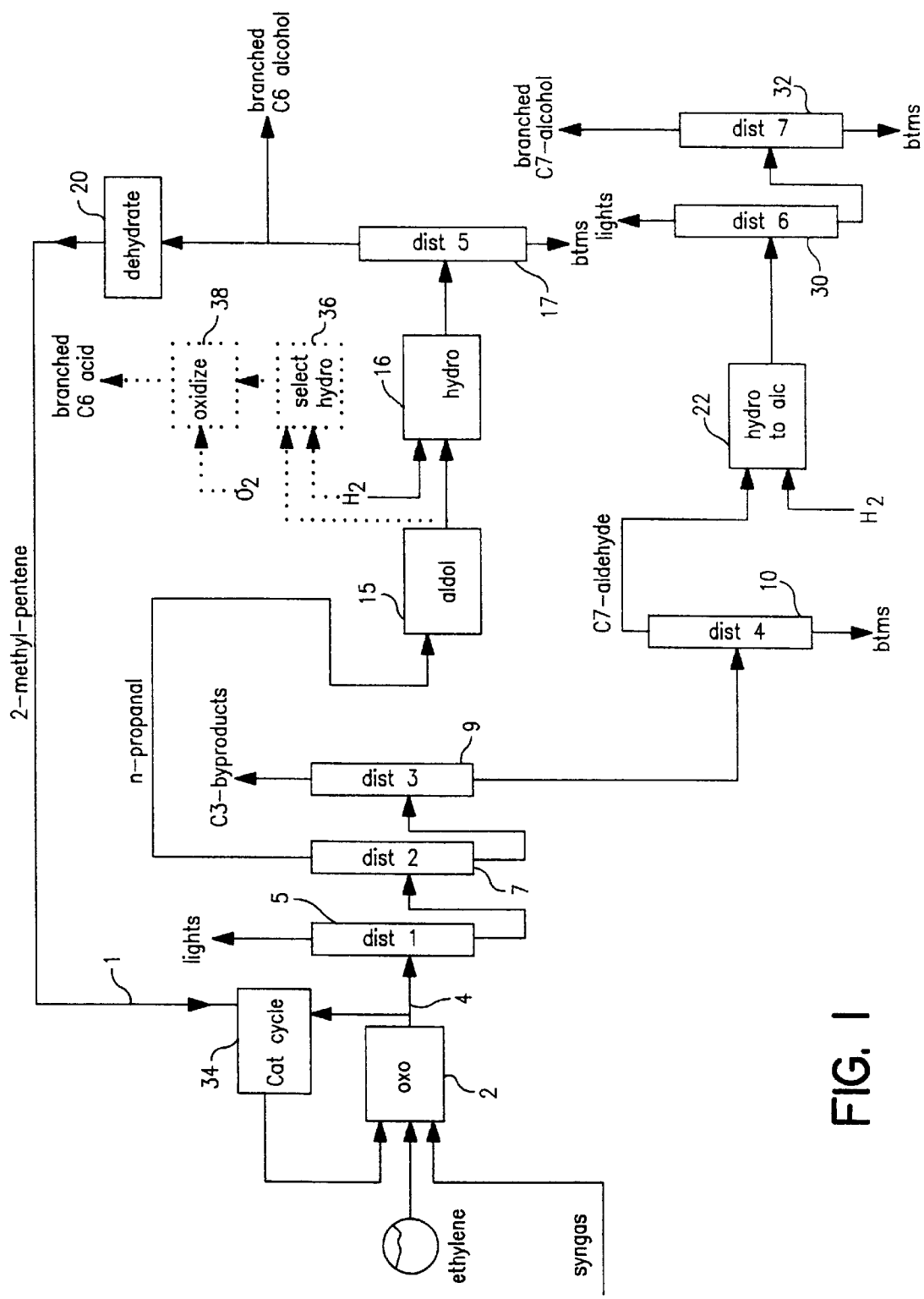
Referring now to FIG. 1, ethylene, syngas and recycled 2-methylpentene are fed to an oxonation reactor 2. A cobalt catalyst is absorbed in the 2-methylpentene feed. The catalyst is separated from the mixed aldehyde product, by contacting it with air in the presence of a light carboxylic acid, sent to an outboard unit 34 and returned to the reactor in the liquid feed. The demetalled product is fed through a line 4 to a first distillation column 5, where lights are taken off overhead and the bottoms product fed to a second distillation column 7. Here, propanal is taken off overhead and the bottoms product fed to a third distillation column 9, where light byproducts are taken off overhead and the bottoms product is fed to a fourth distillation column 10.

The propanal from the second column overhead is fed to an aldol reactor 15, from which the unsaturated $C_6$ aldehyde is fed to a hydrogenation reactor 16. The saturated $C_6$ alcohol-containing product is fed to a fifth distillation column 17, the purified alcohol product being taken off overhead. If desired, part of the alcohol product may be recovered, or it may all be dehydrated in a reactor 20 and fed through a line 1 back to the oxo reactor 2.

From the fourth column 10, $C_7$-aldehyde is taken off overhead and fed to a hydrogenation reactor 22, where it is converted to a $C_7$ alcohol. After passing through a sixth distillation column 30 where it is separated from lights and a seventh distillation column 32, where it is separated from heavies, a branched $C_7$ alcohol is recovered.

The alcohol produced is a mixture of isomers; predominantly, however, it will be 5-methylhexanol and 3-methylhexanol, with minor proportions of 2,4-dimethylpentanol and traces of 2-ethyl-3-methylbutanol.

In broken lines, there is shown an optional additional process in which the product from the aldol reactor 15 is fed to a selective hydrogenation reactor 36 and converted to the corresponding saturated aldehyde, then oxidized by oxygen-enriched air in an oxidation reactor 38 to the corresponding acid. Although shown in FIG. 1 only, the option to take unsaturated aldehydes from the aldol reactor and convert them to the corresponding acids by selective hydrogenation and oxidation is available in all embodiments of the invention, including those subsequently described.

In an alternative procedure, not illustrated, the $C_7$ aldehyde from the column 10 is oxidized, for example with oxygen-enriched air, in an oxidation reactor akin to reactor 38. The acid product from either of these oxidation reactors is desirably distilled to remove lights and heavies.

Figure 2A:
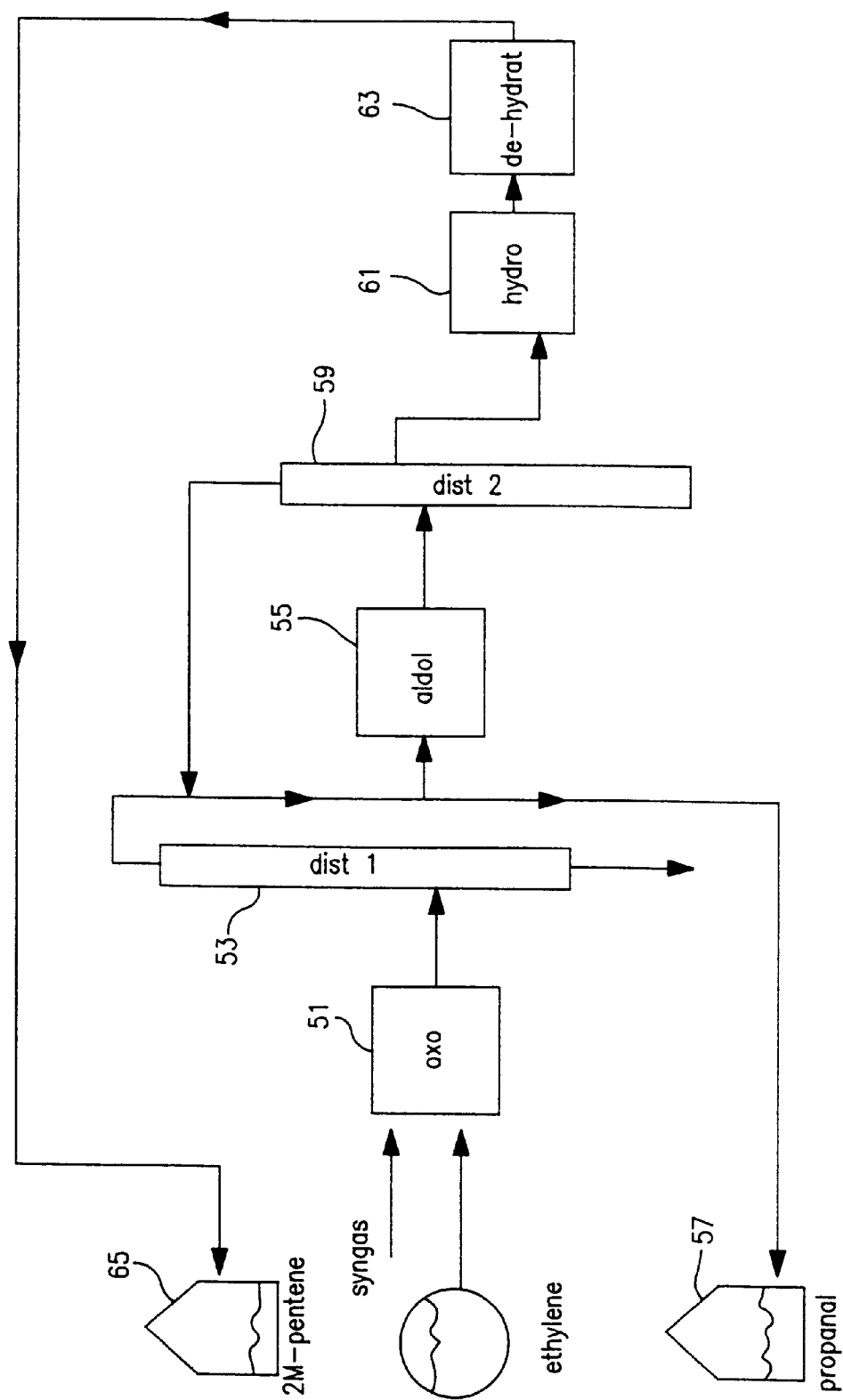
Figure 2B:
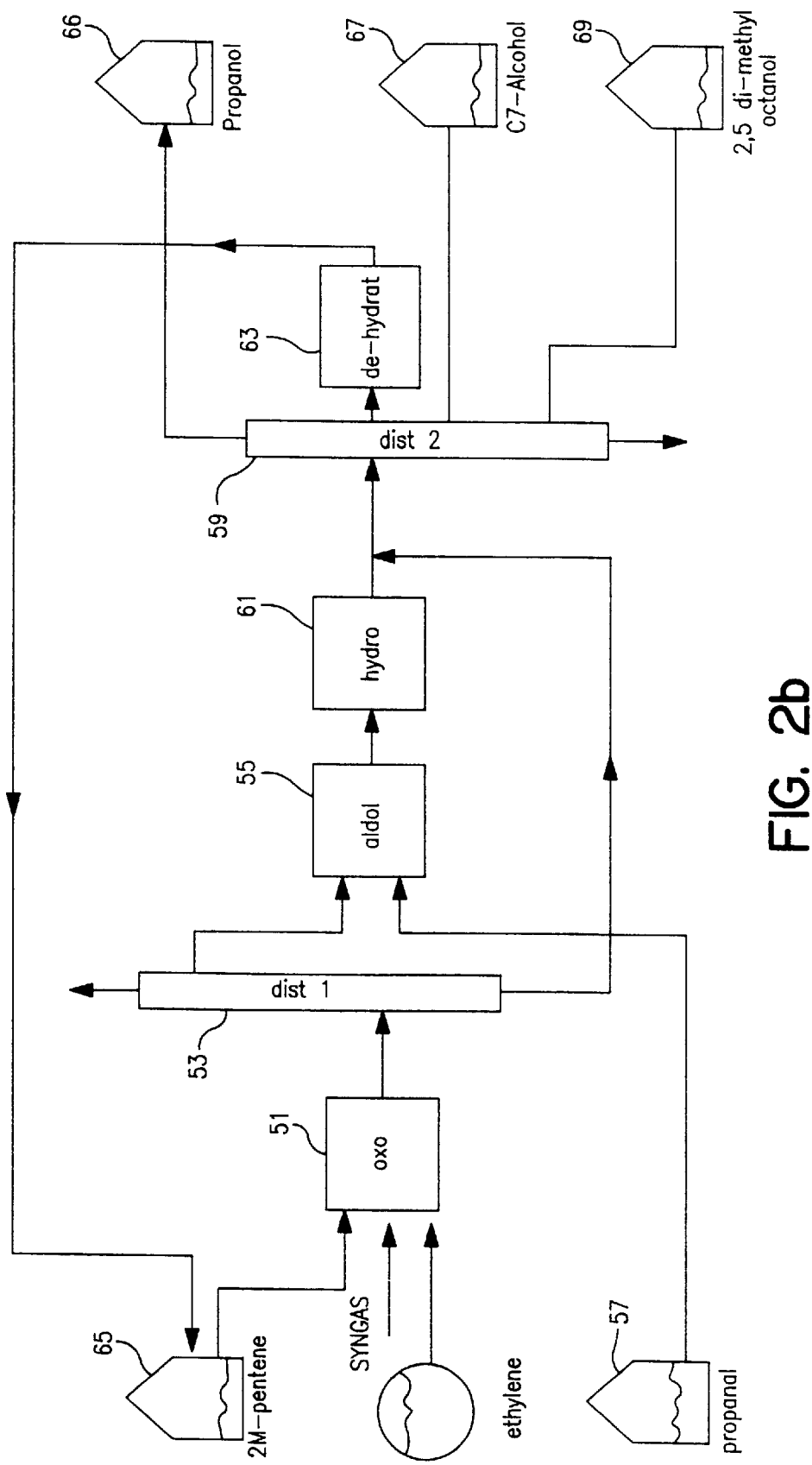

Referring now to FIG. 2, in FIG. 2a, there is shown an example of the process of the second aspect of the invention in its first phase, while FIG. 2b shows its second phase.

In the first phase, the feedstock comprises hydrogen and carbon monoxide (syngas) and ethylene, which feedstock is fed to an oxo reactor 51 together with a cobalt catalyst. Exemplary molar proportions are, per mole of ethylene, 1 to 4 moles of hydrogen and 1 to 2 moles of carbon monoxide, typical conditions being: temperature 100 to 150° C., pressure 20 to 30 MPa, catalyst 0.05 to 0.1% by weight cobalt as hydrido cobalt tetracarbonyl. The reactor product is cooled, degassed, the gases being recycled, and decobalted by contact with air in the presence of an aqueous solution of a light carboxylic acid. The product is then fed to a first distillation column 53, and propanal is recovered overhead. The propanal is divided into portions, a first being fed to an aldol reactor 55, and a second sent to a holding tank 57, the second portion typically representing from 30 to 50% of the total.

The first portion is converted in the reactor 55 (typical conditions: strong base or acid catalyst) to unsaturated $C_6$ aldehydes, primarily 2-methyl-2-pentenal, the product being fed to a second distillation column 59, where unconverted propanal is recycled to the reactor 55, heavies removed as bottoms product, and unsaturated $C_6$ aldehydes taken off as a sidestream and fed to a hydrogenation zone 61 (typical conditions: CuCr catalyst in combination with Ni or Pd catalyst; 120 to 220° C. and medium pressure). The resulting alcohols are then fed to a dehydration unit 63 (typical conditions: alumina catalyst, 200 to 350° C., subatmospheric pressure), and the dehydrated product, hexenes, primarily 2-methylpentene, sent to a holding tank 65.

In the second phase, the feedstock to the oxo reactor 51 comprises syngas and hexenes (the conditions being similar to those used in the first phase except that 0.1 to 0.5% by weight of cobalt catalyst is used) and the desired product, $C_7$ aldehydes, primarily 3-methylhexanal, is recovered as a sidestream from the column 53 and fed, together with propanal from the tank 57, to the aldol reactor 55. As indicated above, the ratio of the feedstreams is selected to maximize unsaturated $C_{10}$ aldehyde production among the product mix of $C_3$ to $C_{14}$ materials. The mixture is fed to the hydrogenation reactor 61, and the resulting alcohol-containing stream is fed to the second column 59 together with, if desired, the bottoms product from the first column 53. From the column 59, propanol is taken overhead to a tank 66, 2-methylpentanol is taken as a first sidestream to dehydration unit 63 and thence to a tank 65, $C_7$ alcohols (primarily 3-methylhexanol) are taken as a second sidestream to a tank 67, and $C_{10}$ alcohols, primarily 2,5-dimethyloctanol, taken as a third sidestream to a tank 69.

This second phase is continued until the supplies from tanks 57 and 65 are exhausted, when the process is switched back to the first phase.

Figure 3:
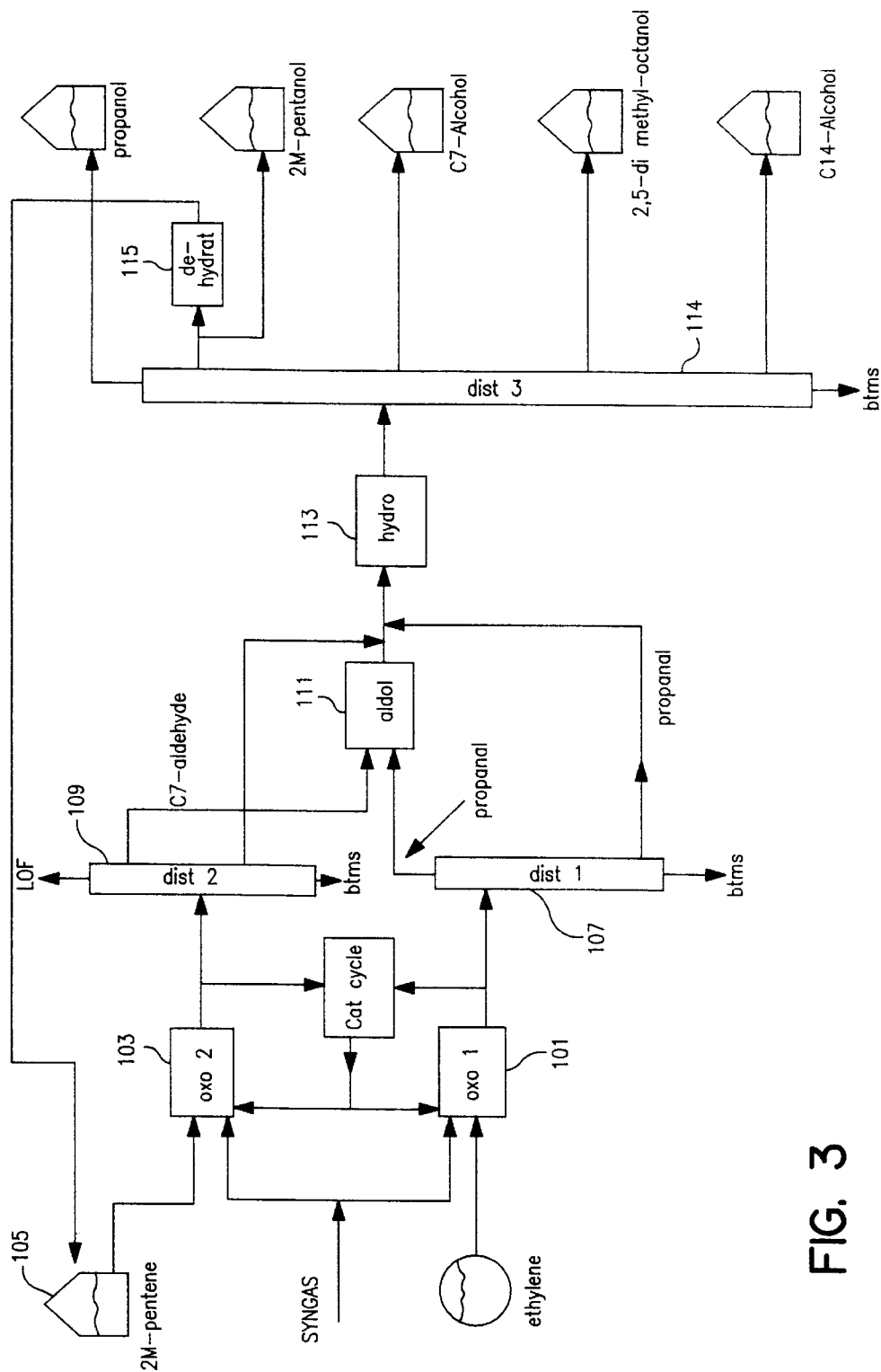

Referring now to FIG. 3, into first and second oxonation reactors 101 and 103, syngas and catalyst are fed. Into the first reactor 101 the feedstock is ethylene, while 2-methylpentene is fed from a storage tank 105 to the second reactor 103. The propanal-containing product from the first reactor 101 is demetalled and fed to a first distillation column 107, pure propanal being taken off overhead and any propanol being taken off as a sidestream. Similarly, a $C_7$ aldehyde-containing product is passed from the reactor 103 to a second distillation column 109, any $C_7$ alcohol being taken off as a second sidestream. The aldehydes are fed to an aldol reactor 111, the unsaturated aldehyde product then being hydrogenated, together with the alcohol-containing sidestreams, in a hydrogenation unit 113. The alcohol product from the unit 113 is passed to a further distillation column or columns represented schematically by column 114 where it is separated. Reference numeral 114 may represent a batch procedure in which products are recovered sequentially. When 2-methylpentanol is taken off it is divided, and a portion passed to a dehydration unit 115, the resulting 2-methylpentene being recycled to the storage tank 105. $C_7$, $C_{10}$ and $C_{14}$ alcohols are taken off subsequently. Alternatively, more than one column may be used, either sequentially or making a first heart cut and separating individual cuts.

Figure 4:
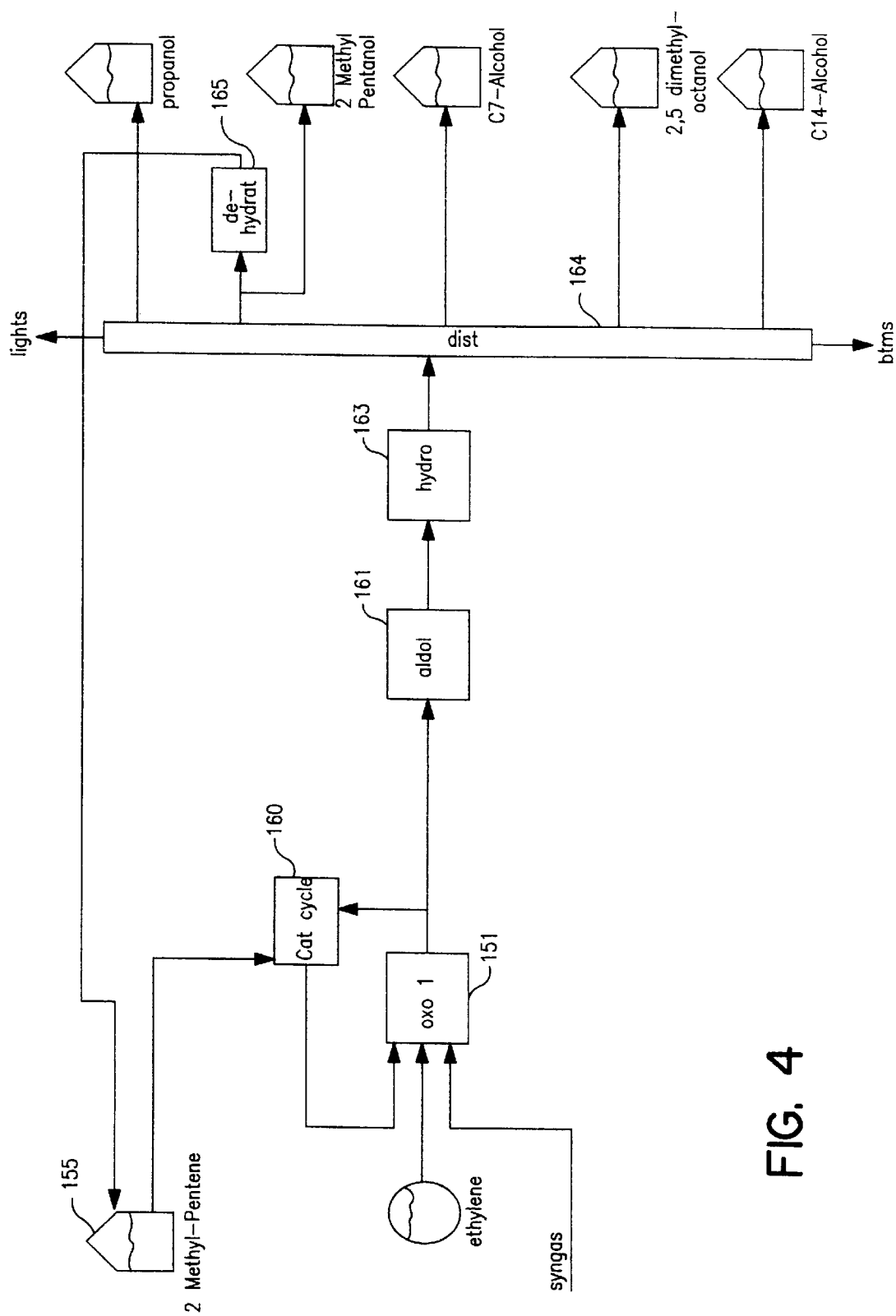

Referring now to FIG. 4, the procedure is generally similar to that of FIG. 3, with the exception that a single oxonation reactor 151 is used, and that catalyst is returned to the reactor from an outboard unit 160 by being entrained in the 2-methylpentene from a storage tank 155. Treatment in aldol reactor 161, hydrogenation unit 163, distillation column 164, dehydration unit 165, and recycling of 2-methylpentene to the storage tank 155 are identical to that described above for FIG. 3.

Figure 5:
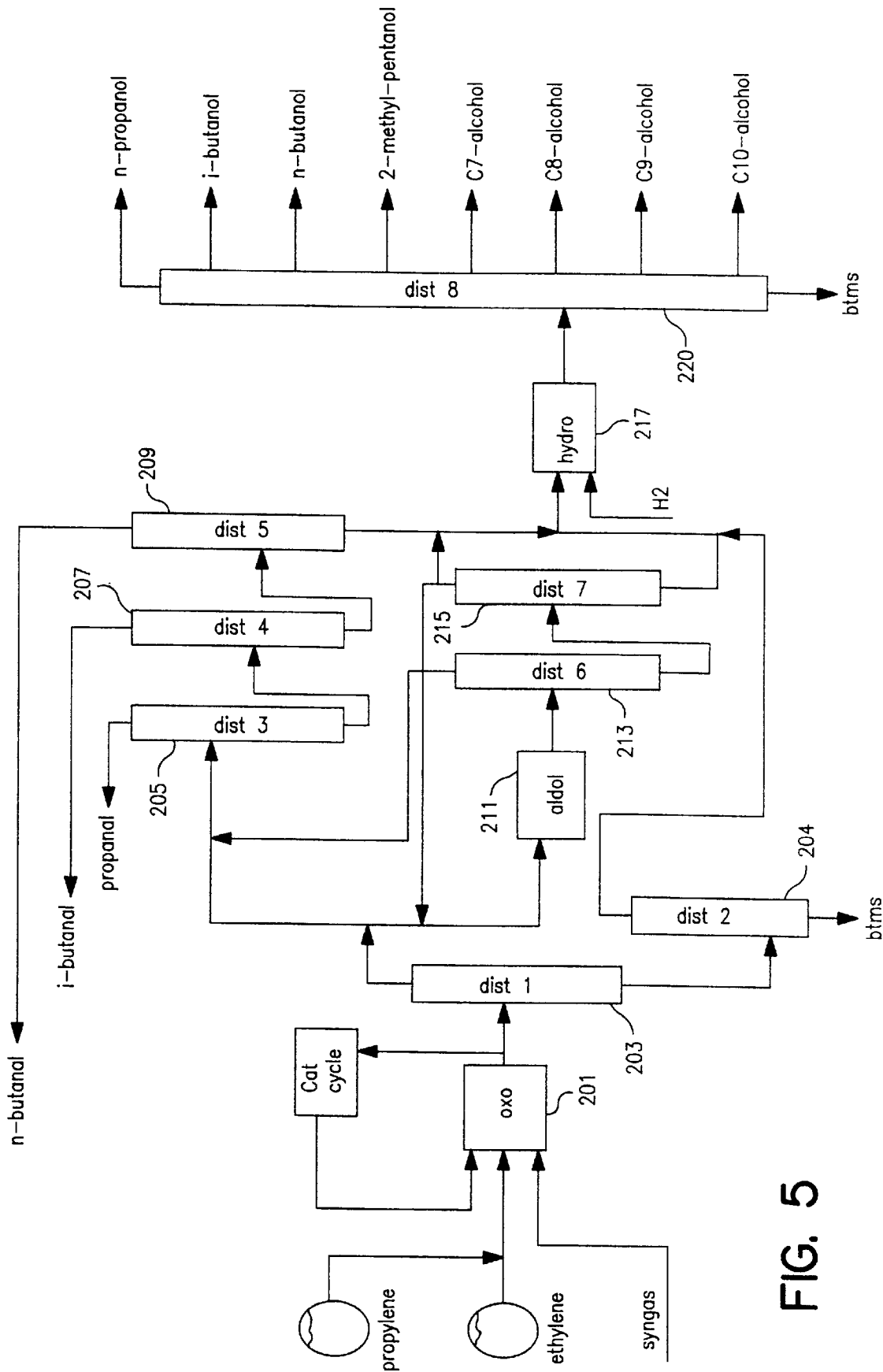

Referring now to FIG. 5, into a single oxonation reactor 201 are fed syngas, ethylene, propene, and catalyst, examples of typical conditions and reaction proportions being ethylene:propene—1:10 to 10:1 by weight, $H_2$/CO syngas ratio 0.5:1 to 2:1, low or high pressure Rh catalysis or high pressure Co catalysis, with a heavy diluent for temperature control, as catalyst carrier, or both. After the oxo product is demetalled and degassed, also removing light olefins and paraffins, the product is fed to a first distillation column 203. Here all light aldehydes are taken off overhead. When a substantial quantity of alcohol is being formed in the reactor 201, the bottoms product of the column 203 may be worked up in a second column 204 where it is separated from any heavy diluent and heavies formed in the oxonation reaction. Part of the overhead stream from the column 203 is passed to three further distillation columns, 205, 207, and 209, whence, respectively, propanal, i-butanal and n-butanal are recovered overhead.

A second part of the light aldehyde stream is fed to an aldolization reactor 211, the aldol product being fed to a sixth distillation column 213. The overhead from this distillation column 213, containing unreacted light aldehydes, may be fed to the third distillation column 205 or recycled, while the bottoms product is passed to the seventh column 215. From here, the overhead may be recycled or mixed with the bottoms product from the fifth column 209, which is mixed with the bottoms product from the seventh column 215 which is being fed to a hydrogenation unit 217 as is the overhead product from the second column 204. The hydrogenation product is then fed to an eighth distillation section 220, whence a variety of alcohols from $C_3$ to $C_{10}$, with the exception of $C_5$, is recovered. The section 220 may be a single column, using batch operation, or multiple columns, operated continuously, either in a sequential operation or by making a first heart cut, followed by separation of individual cuts.

The preponderant isomers of the $C_7$ to $C_{10}$ alcohols are
$C_7$:2,4-dimethylpentanol, 2-ethylpentanol, 2-methylhexanol
$C_8$:2-ethylhexanol, 2-ethyl-4-methylpentanol
$C_9$:2,4-dimethylheptanol
$C_{10}$:2-ethyl-4-methylheptanol.

Figure 6:
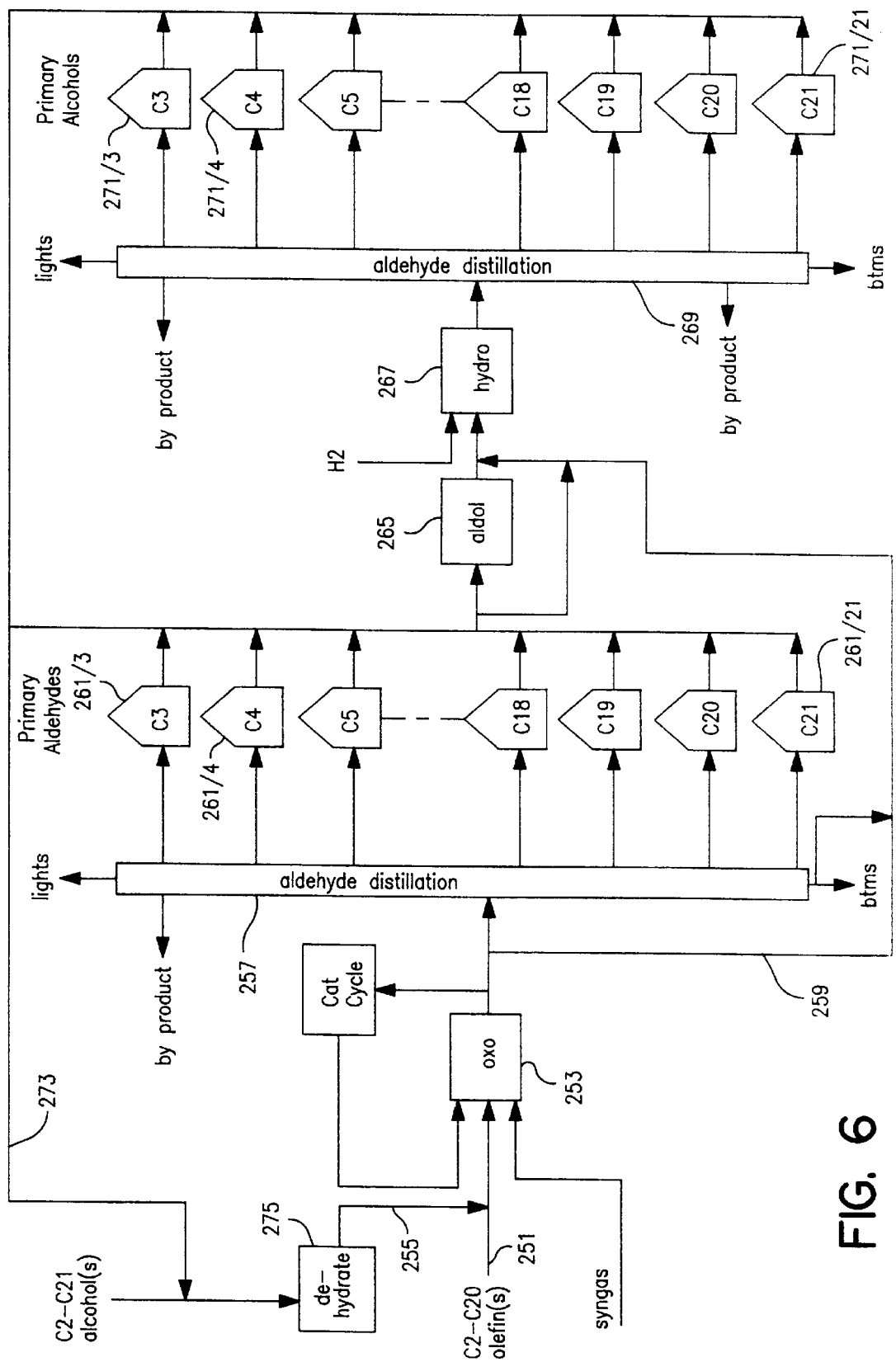

Referring now to FIG. 6, at least one olefin is fed by a line 251 to an oxonation reactor 253, where it is caused to react with syngas. The olefin is fed in admixture with a further olefin or olefins from a line 255. Part of the resulting aldehyde product mixture is passed to a distillation column 257, a second part optionally being taken off through a line 259. The separated aldehyde products are passed to two or more of storage tanks 261/3 to 261/21, as appropriate to the boiling point or range, unreacted material being taken off overhead, and the bottoms optionally fed to the line 259. Material from one or more of the tanks 261 is fed to an aldolization reactor 265, a part optionally being fed to the line 259. Aldolization product is fed to a hydrogenation unit 207 together with any content of the line 259, and the hydrogenation product fed to a second distillation column 269. The separated alcohols are passed to one or more of storage tanks 271/3 to 271/21, whence product may be recovered. As required, the contents of one or more of the tanks 271 may be fed through a line 273 to a dehydration unit 275, where it may be combined as required with alcohol from a separate source. The resulting olefin is fed by the line 255 to oxonation.

What is claimed is:

1. A process for the manufacture of at least one higher aldehyde, said process comprising:

hydroformylating ethylene and a second ethylenically unsaturated hydrocarbon to form a composition containing propionaldehyde and a second aldehyde, wherein said second aldehyde contains less than 2 hydrogen atoms bonded to the alpha carbon atom; and subjecting the propionaldehyde and second aldehyde containing composition to cross-aldolization to form a cross-aldplization product, wherein at least a portion of said propionaldehyde undergoes cross-aldolization with said second aldehyde and said cross-aldolization product further undergoes dehydration to produce an unsaturated aldehyde.

2. A process as claimed in claim 1, wherein the ethylene and second ethylenically unsaturated hydrocarbon are hydroformylated in admixture to give a composition comprising propionaldehyde and the second aldehyde.

3. A process as claimed in claim 1, wherein said second ethylenically unsaturated hydrocarbon is a $C_6$ to $C_{12}$ olefin.

4. A process for the manufacture of organic compounds, comprising:

hydroformylating a composition comprising ethylene and 2-methylpentene;

separating a portion of the resulting $C_3$ aldehyde and $C_7$ aldehydes;

cross-aldolizing at least a portion of the $C_3$ aldehyde and $C_7$ aldehydes followed by dehydration to form a composition comprising an unsaturated $C_6$ aldehyde and $C_{10}$ aldehydes;

hydrogenating at least a portion of the resulting $C_6$ and $C_{10}$ unsaturated aldehyde composition to form a composition comprising the corresponding alcohols;

separating at least a portion of the $C_6$ alcohol from the alcohol composition;

dehydrating the $C_6$ alcohol to form a composition comprising 2-methylpentene;

returning the 2-methylpentene comprising composition to the hydroformylation stage; and recovering a product comprising a $C_7$ aldehyde.

5. A process as claimed in claim 4, further comprising selectively hydrogenating a further portion of the unsaturated $C_6$ aldehyde to a saturated $C_6$ aldehyde.

6. A process as claimed in claim 5, wherein at least a portion of said saturated $C_6$ aldehyde is oxidized to form a carboxylic acid.

7. A process for the manufacture of an alcohol, comprising:

(a) subjecting ethylene to hydroformylation conditions to form propionaldehyde;

(b) subjecting a first portion of the propionaldehyde to aldol condensation followed by dehydration to form an unsaturated $C_6$ aldehyde;

(c) hydrogenating the unsaturated $C_6$ aldehyde resulting from aldol condensation to form a $C_6$ alcohol;

(d) dehydrating the $C_6$ alcohol to form a $C_6$ unsaturated hydrocarbon;

(e) subjecting a composition comprising the $C_6$ unsaturated hydrocarbon, carbon monoxide, and hydrogen to hydroformylation conditions to form a composition comprising a saturated $C_7$ aldehyde;

(f) subjecting the saturated $C_7$ aldehyde and a second portion of propionaldehyde to cross-aldolization, wherein the cross-aldolization product further undergoes dehydration to produce an unsaturated aldehyde; and (g) hydrogenating the unsaturated cross-aldolization aldehyde product to form a higher alcohol.

8. A process as claimed in claim 7, wherein said higher alcohol is esterified.

9. A semi-continuous process for the manufacture of an alcohol, comprising:

(a) alternately subjecting ethylene and an unsaturated $C_6$ olefin to hydroformylation conditions to form propionaldehyde and a saturated $C_7$ aldehyde;

(b) subjecting a first portion of the propionaldehyde to aldol condensation followed by dehydration to form an unsaturated $C_6$ aldehyde;

(c) hydrogenating the unsaturated $C_6$ aldehyde resulting from aldol condensation to form a $C_6$ alcohol;

(d) dehydrating the $C_6$ alcohol to form a $C_6$ unsaturated hydrocarbon;

(e) recycling the $C_6$ unsaturated hydrocarbon to hydroformylation step a;

(f) subjecting the saturated $C_7$ aldehyde produced in step a and a second portion of propionaldehyde to cross-aldolization, wherein the cross-aldolization product further undergoes dehydration to produce an unsaturated aldehyde; and (g) hydrogenating the unsaturated cross-aldolization aldehyde product to form a higher alcohol.

10. A process as claimed in claim 1, comprising:

separately hydroformylating the ethylene and the second ethylenically unsaturated hydrocarbon;

combining the resulting compositions comprising the propionaldehyde and second aldehyde;

subjecting the combined compositions to cross-aldolization, followed by dehydration; and hydrogenating the unsaturated cross-aldolization aldehyde product to form a higher alcohol.

11. A process as claimed in claim 1, wherein said cross-aldolization product reaction is accompanied by a self-aldol condensation of the said propionaldehyde, said process further comprising:

hydrogenating said cross-aldolization product to form a composition comprising alcohols; and separating the resulting alcohols.

12. A process as claimed in claim 11, further comprising dehydrating the alcohol derived from the self-aldolization of the propionaldehyde and returning the resulting ethylenically unsaturated hydrocarbon to hydroformylation.

13. A process as claimed in claim 1, wherein the ethylene and second ethylenically unsaturated hydrocarbon are hydroformylated in admixture, the propionaldehyde and second aldehyde are at least partially separated, further comprising:

hydrogenating the unsaturated aldehyde resulting from dehydration to form saturated alcohols;

separating the resulting saturated alcohols at least partially;

dehydrating at least one saturated alcohol to a third erhylenically unsaturated hydrocarbon; and hydroformylating said third ethylenically unsaturated hydrocarbon to a third aidehyde.

14. A process as claimed in claim 1, wherein only a portion of the composition comprising propionaldehyde and second aldehyde is fed to aldolization, and a further portion is fed to distillation to yield separate compositions comprising the individual aldehydes.

15. A process as claimed in claim 1, wherein hydroformylation is carried out in the presence of a cobalt catalyst.

16. A process as claimed in claim 8, wherein the ester is made by reaction with a dibasic acid or an anhydride thereof.

17. A process as claimed in claim 1, wherein a portion of the resulting self condensation product of propionaldehyde is returned to the aldolization zone.

18. A process as claimed in claim 1, further comprising selectively hydrogenating a portion of the unsaturated second aldehyde to form a corresponding saturated higher aldehyde and oxidizing the saturated higher aldehyde to form a corresponding higher acid.

* * * * *